United States Patent [19]

Fabre et al.

[11] Patent Number: 5,441,980
[45] Date of Patent: Aug. 15, 1995

[54] POTENTIALIZATION OF PYRETHROID BY CROTAMITON WHICH IS USEFUL IN THE TREATMENT OF PEDICULOSIS

[75] Inventors: Pierre Fabre; Gilbert Mouzin, both of Castres; Michel JeanJean, Castanet-Tolosan; Nicole Monteny, Orsay; Henri Cousse, Castres, all of France

[73] Assignee: Pierre Fabre Sante, Boulogne, France

[21] Appl. No.: 46,797

[22] Filed: Apr. 16, 1993

[30] Foreign Application Priority Data

Apr. 16, 1992 [FR] France .................. 92 04691

[51] Int. Cl.⁶ .................................... A01N 53/08
[52] U.S. Cl. ...................... 514/531; 514/627
[58] Field of Search .................... 514/531, 627

[56] References Cited

U.S. PATENT DOCUMENTS 5,064,859  11/1991  Crammer et al. ............... 514/560
5,292,504  3/1994   Cardin et al. .................... 424/70

FOREIGN PATENT DOCUMENTS 638662    6/1950   United Kingdom .
WO91/15953 10/1991  WIPO .

OTHER PUBLICATIONS

Chemical Patents Index, Documentation Abstracts Journal, Derwent Publications Ltd., Aug. 28, 1985, AN-85-159610/27, DD-A-219 374, Mar. 6, 1985.
Biological Abstracts, vol. 93, No. 10, May 15, 1992, AN-117282, R. Hatsushika, et al., "Case Studies on Sting Dermatitis by Bethylid Wasp, Cephalonomia Gallicola (Ashmead, 1987) (Hymenoptera:Bethylidae) Found in Okyama, Japan".
Biological Abstracts, vol. 93, No. 4, Feb. 15, 1992, AN-38025, R. S. Purvis, et al., "An Outbreak of Lindane-Resistance Scabies Treated Successfully with Permethrin 5 Percent Cream".

Primary Examiner—Allen J. Robinson
Attorney, Agent, or Firm—Oblon, Spivak, McClelland, Maier, & Neustadt

[57] ABSTRACT

The present invention relates to a dermatological and/or cosmetological composition which is useful in the treatment of pediculosis, characterized in that it contains a synergic combination of a pyrethroid and of crotamiton.

The pyrethroids which are the subject of this composition are more particularly permethrin, bioallethrin, resmethrin, tetramethrin and deltamethrin.

3 Claims, No Drawings

POTENTIALIZATION OF PYRETHROID BY CROTAMITON WHICH IS USEFUL IN THE TREATMENT OF PEDICULOSIS

The subject of the present invention is a synergic combination of pyrethroids and crotamiton and their useful formulation for destroying ectoparasites such as lice and their nits.

The pediculicides currently marketed display resistance phenomena on lice and more particularly on nits. In 1945, the development of insecticidal powders based on DDT was the subject of the first campaign against lice. It was only in 1952 that the first signs of resistance of the body louse to DDT appeared in Korea (Hurlbut et al., Science, 115, Nov. 12, 1952).

The louse has also become resistant to carbaryl (Clark et al., J. Econ. Ent., 60, 2, 398, 1967) and to malathion (Cole, J. Econ. Ent., 66, 1, p. 118, 1973).

The head louse is described as resistant to DDT in France from 1976 (Lamizana, Med. Mal. Infectieuses, 6.2, p. 48, 1976). According to Combescot and Coz, this resistance phenomenon would currently apply to the derivatives of the pyrethroid class which are the most widely used products as pediculicides.

The simultaneous use of two or more pediculicides, having different physiological modes of action, should constitute a treatment which would have high probabilities of avoiding the possibilities of resistant population selection.

The subject of the present invention relates to a dermatological and/or cosmetological composition which is useful for the treatment of pediculosis comprising a synergic combination of at least one pyrethroid with crotamiton.

The amount of crotamiton by weight is advantageously 10 to 100 times greater than that of the pyrethroid, or of the pyrethroid mixture.

The main pyrethroids are:
bioallethrin
resmethrin
tetramethrin
D-phenothrin
and deltamethrin.

Preferentially, the pyrethroid is chosen from permethrin, bioallethrin, tetramethrin, deltamethrin and their mixtures.

The composition according to the present invention preferably contains from 0.01 to 1% by weight of pyrethroid. It also advantageously contains between 0.1 and 10% by weight of crotamiton.

Preferentially, the dermatological and/or cosmetological composition according to the present invention comprises:
a) 0.01 to 1% by weight of a pyrethroid chosen from bioalletrin, resmethrin, tetramethrin, D-phenothrin, permethrin, deltamethrin and their mixtures,
b) 0.1 to 10% by weight of crotamiton,
c) 0 to 70% by weight of a surface-active agent,
d) 0 to 50% by weight of an organic solvent chosen from lower aliphatic alcohols, silicones, deodorized petroleum oil and their mixtures,
e) 0 to 4% by weight of a foaming agent,
f) a fragrance,
g) a preserving agent, and made up to 100% with water.

The surface-activate agent is chosen from anionic, nonionic, cationic or amphoteric surface-active agents and their mixtures.

As non-limiting examples, we describe a study of the permethrin and crotamiton combination which exhibits an entirely surprising potentialization of the nitkilling action. This work was carried out in the Laboratoire de Lutte contre les Insectes Nuisibles (L. I. N.) [Laboratory for Controlling Harmful Insects] of the Centre Orstom at Bondy under the responsibility of Dr. Monteny.

1. Method

The experiments were carried out on Pediculus humanus nits arising from a strain raised on rabbits of the race "New Zealand".

The nits, aged from 2 to 5 days, fixed to woven supports, are immersed in successive dilutions of products made in a solution containing 5% acetone, 45% absolute alcohol and 50% water. The concentrations expressed in this study are calculated in volume of crude product/volume of solvent. The nits, counted on their woven support, are left in contact for three minutes, rinsed with water three times, dried and then placed in an oven at 28° C. and at 70% relative humidity.

Each day, the nits are placed on the shaven stomach of a rabbit and the hatchings are recorded. The hatchings are spaced out. The reading day is that on which the maximum hatching is observed; the number of young living lice retained corresponds to the number of those which gorge themselves. At this stage, the number of open nits (hatched) is noted.

2. Determination of the Mortality/Concentration Curves 2.1 Permethrin

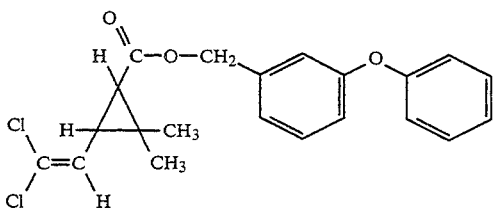

Permethrin is used as a pesticide in agriculture and as an insecticide in veterinary medicine; it was approved by the FDA in 1986 for the local treatment of pediculosis of the scalp (Nix cream rinse, Burroughs Wellcom, U.S.A., concentration 1%). In France, permethrin has been marketed since 1978 (Pyreflor - Lab. Clement).

Permethrin destroys both the lice and the nits; it acts on the nervous system of insects but its mechanism of action is not completely elucidated. In mammals, this active ingredient is only slightly absorbed and inactivated by esterases.

2.1.1. Results

The percentages of hatchings obtained with permethrin and the controls are carried in Tables I and II. The test was repeated in order to obtain a reliable and repetitive base for objectivizing the true potentialization of the subsequent combination of the study.

The percentages of hatchings are recorded as H % and the percentages of insects which feed as F % (the actual number between parentheses).

TABLE I

Activity of PM 5 in acetone/alcohol solution
Eggs from 2 to 5 August 1991
Test on 7 August 1991

| | Dry control | Solvent control | Dilution (%) | | | | |
|---|---|---|---|---|---|---|---|
| | | | 0.5 | 0.25 | 0.125 | 0.0625 | 0.0312 |
| H % | 95.2 | 87.2 | 1.96 | 12.25 | 39.56 | 58.26 | 77.48 |
| | (104) | (94) | (153) | (155) | (91) | (115) | (111) |
| F % | 94.23 | 82.98 | 0.0 | 7.1 | 30.77 | 45.22 | 73.87 |

TABLE II

Activity of PM 5 in acetone/alcohol solution
Eggs from 16 to 19 August 1991
Test on 21 August 1991

| | Dry control | Solvent control | Dilution (%) | | | | |
|---|---|---|---|---|---|---|---|
| | | | 0.5 | 0.25 | 0.125 | 0.0625 | 0.0312 |
| H % | 83.1 | 83.1 | 0.0 | 9.9 | 42.6 | 53.1 | 86.1 |
| | (83) | (71) | (80) | (101) | (122) | (96) | (72) |
| F % | 80.72 | 76.06 | 0.0 | 6.93 | 31.15 | 45.83 | 69.44 |

2.1.2. Determination of the Lethal Concentrations

The $LC_5$, $LC_{10}$, $LC_{20}$, $LC_{30}$, $LC_{40}$ and $LC_{50}$ values were determined overall by summing the two series of results by virtue of a Probit mortality analysis program.

Probits Analysis Program

PM 5 ( Permethrin )
The concentrations are in: %
Number of control insects: 165
Mortality in the control : 21

| Points | Concentrations | Crude Mortality in % | Corrected Mortality | Calculated Probits |
|---|---|---|---|---|
| 1 | 0.5 | 100.0 | 100.0 | 7.59 |
| 2 | 0.25 | 92.97 | 92.0 | 6.41 |
| 3 | 0.125 | 69.01 | 64.9 | 5.37 |
| 4 | 0.0625 | 54.5 | 48.4 | 4.96 |
| 5 | 0.0312 | 27.87 | 18.3 | 4.09 |

The $LC_5$ is equal to: 0.015% Confidence interval: 0.012–0.019
The $LC_0$ is equal to: 0.022% Confidence interval: 0.018–0.026
The $LC_{20}$ is equal to: 0.035% Confidence interval: 0.03–0.039
The $LC_{30}$ is equal to: 0.046% Confidence interval: 0.041–0.051
The $LC_{40}$ is equal to: 0.06% Confidence interval: 0.055–0.066
The $LC_{50}$ is equal to: 0.072% Confidence interval: 0.066–0.078

Equation of the weighted regression line:

$$Y = 2.55X + 2.81$$

The x2 corresponding to a probability of 5% is: 7.815
The x2 is 13.167. It is thus significant.

2.2. Crotamiton

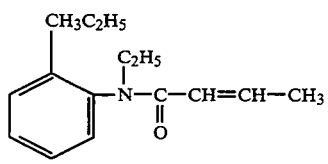

Crotamiton has been marketed in France since 1949 under the tradename Eurax by the company Ciba Geigy with as indication: antipruriginous. In the U.S.A., the company Weswood also markets it as an antipruriginous agent but also with a scabicidal indication. The mechanism of action of this active ingredient is not known.

2.2.1 Results

The percentages of hatchings obtained with the product CR 3 and their controls are carried in Tables III, IV and V.

The percentages of hatchings are recorded as H %, and the percentages of the insects which feed as F % (the actual number between parentheses).

TABLE III

Activity of CR 3 in acetone/alcohol solution
Eggs from 12 to 15 July 1991
Test on 17 July 1991

| | Solvent control | Dilution (%) | | | | |
|---|---|---|---|---|---|---|
| | | 3 | 2 | 1 | 0.5 | 0.25 |
| H % | 63.9 | 1.6 | 45.0 | 61.4 | 65.8 | 34.8 |
| | (119) | (122) | (131) | (101) | (111) | (89) |
| F % | 58.82 | 1.64 | 39.69 | 59.41 | 58.56 | 32.58 |

TABLE IV

Activity of CR 3 in acetone/alcohol solution
Eggs from 2 to 5 August 1991
Test on 7 August 1991

| | Dry control | Solvent control | Dilution (%) | | | | |
|---|---|---|---|---|---|---|---|
| | | | 3 | 2.5 | 2 | 1.5 | 1 |
| H % | 97.0 | 74.4 | 0.99 | 52.0 | 71.4 | 74.0 | 75.0 |
| | (68) | (82) | (101) | (123) | (119) | (69) | (76) |
| F % | 91.18 | 67.07 | 0.0 | 23.58 | 66.39 | 62.32 | 68.42 |

TABLE V

Activity of CR 3 in acetone/alcohol solution
Eggs from 16 to 19 August 1991
Test on 21 August 1991

| | Dry control | Solvent control | Dilution (%) | | | | |
|---|---|---|---|---|---|---|---|
| | | | 3 | 2.5 | 2 | 1.5 | 1 |
| H % | 91.7 | 73.8 | 0.88 | 2.6 | 35.8 | 48.0 | 71.8 |
| | (72) | (126) | (113) | (114) | (120) | (77) | (78) |
| F % | 88.89 | 70.63 | 0.0 | 1.75 | 25.83 | 40.26 | 62.82 |

Table V: Activity of CR 3 in acetone/alcohol solution Eggs from 16 to 19 August 1991 Test on August 21, 1991

Comment: The three series of results are repetitive. They are all taken into account for calculating the lethal concentrations.

2.2.2. Determination of Lethal Concentrations

The $LC_5$, $LC_{10}$, $LC_{20}$, $LC_{30}$, $LC_{40}$ and $LC_{50}$ values were determined overall by summing the three series of results by virtue of a Probit mortality analysis program.

Probit Analysis Program

CR 3 (Crotamiton)
The concentrations are in: %
Number of control insects: 327
Mortality in the control : 31

| Points | Concentrations | Crude Mortality in % | Corrected Mortality | Calculated Probits |
|---|---|---|---|---|
| 1 | 3.0 | 99.4 | 99.3 | 6.38 |
| 2 | 2.5 | 98.25 | 98.1 | 6.28 |

-continued

| Points | Concentrations | Crude Mortality in % | Corrected Mortality | Calculated Probits |
|---|---|---|---|---|
| 3 | 2.0 | 70.05 | 66.7 | 5.43 |
| 4 | 1.5 | 59.74 | 55.3 | 5.13 |
| 5 | 1.0 | 36.91 | 29.9 | 4.49 |

The $LC_5$ is equal to: 0.534% Confidence interval: 0.46-0.604

The $LC_{10}$ is equal to: 0.668% Confidence interval: 0.589-0.74

The $LC_{20}$ is equal to: 0.882% Confidence interval: 0.802-0.955

The $LC_{30}$ is equal to: 1.043% Confidence interval: 0.964-1.114 The $LC_{40}$ is equal to: 1.233% Confidence interval: 1.158-1.302

The $LC_{50}$ is equal to: 1.378% Confidence interval: 1.306-1.446

Equation of the weighted regression line: $Y = 4.13X - 3.84$

The x2 [sic]corresponding to a probability of 5% is: 7.815

The x2 [sic]is 15.774. It is thus significant.

2.3 Permethrin/Crotamiton Combination

The percentages of hatchings obtained with the product PM 5 at $LC_5$, with product CR 3 added at $LC_5$, $LC_{10}$, $LC_{20}$, and $LC_{30}$, and the controls are carried in Table VI.

The percentages of hatchings are recorded as H % and the percentages of insects which feed as F % (the actual number between parentheses).

TABLE VI

Activity of PM 5 at $LC_5$ in acetone/alcohol solution, to which CR 3 has been added at $LC_5$, $LC_{10}$, $LC_{20}$, $LC_{30}$ and $LC_{40}$
Eggs from 15 to 18 November 1991
Test on 20 November 1991

| | Dry Control | Solvent control | PM 5 $LC_5$ | | | |
|---|---|---|---|---|---|---|
| | | | CR 3 $LC_{30}$ | CR 3 $LC_{20}$ | CR 3 $LC_{10}$ | CR 3 $LC_5$ |
| H% | 82.42 | 79.78 | 0.0 | 1.11 | 2.97 | 3.06 |
| | (91) | (89) | (124) | (90) | (101) | (98) |
| F% | 58.24 | 69.66 | 0.0 | 0.0 | 0.0 | 0.0 |

Table VI: Activity of PM 5 at $LC_5$ in acetone/alcohol solution, to which CR 3 has been added at $LC_5$, $LC_{10}$, $LC_{20}$, $LC_{30}$ and $LC_{40}$
Eggs from 15 to 18 November 1991
Test on 20 November 1991

The percentages of hatchings obtained with the product CR 3 at $LC_5$, with product PM 5 added at $LC_5$, $LC_{10}$, $LC_{20}$ and $LC_{30}$, are carried in Table VII.

The percentages of hatchings are recorded as H % and the percentages of insects which feed at F % (the actual number between parentheses).

TABLE VII

Activity of CR 3 at $LC_5$ in acetone/alcohol solution with PM 5 added at $LC_5$, $LC_{10}$, $LC_{20}$ and $LC_{30}$
Eggs from 15 to 18 November 1991
Test on 20 November 1991

| | CR 3 $LC_5$ | | | |
|---|---|---|---|---|
| | PM 5 $LC_{30}$ | PM 5 $LC_{20}$ | PM 5 $LC_{10}$ | PM 5 $LC_5$ |
| H % | 0.0 | 1.74 | 0.79 | 3.06 |
| | (125) | (115) | (126) | (98) |
| F % | 0.0 | 0.0 | 0.0 | 0.0 |

Table VII: Activity of CR 3 at $LC_5$ in acetone/alcohol solution with PM 5 added at $LC_5$, $LC_{10}$, $LC_{20}$ and $LC_{30}$
Eggs from 15 to 18 November 1991
Test on November 20, 1991
2.3.1. Results The study carried out at the LIN had the object:

a) of determining with precision the conditions of reproducibility of measuring the effects of permethrin and of crotamiton on Pediculus humanus.

b) from the concentration/mortality relationship for each of the two products, to define the optimum composition of a mixture, while searching for a synergic effect.

It appeared, during the preliminary tests, that the most reproducible value, from the biological parameters available a priori, was the percentage of young lice which feed after hatching with respect to the number of nits introduced into the test.

Successive tests have attempted to define the optimum composition of the mixture by combining concentrations leading to partial mortalities. If the resulting mortality is greater than the sum of the two partial mortalities, a synergic effect may be expected.

This study has surprisingly shown a very strong potentialization of these two molecules. A mortality of 100% is achieved by combining crotamiton and permethrin at a concentration which is supposed to give 5% mortality for each of the products. We thus obtain a formulation having a synergic effect of more than 10 times the result expected by additivity of action (i.e. 5%+5% =10%).

The coefficient of potentialization by crotamiton was precisely determined from the ratio of the values of the lethal doses 50.

The lethal dose 50 of permethrin is 0.072%.

The lethal dose 50 of the crotamiton/ permethrin mixture is 4.228%, which corresponds to a true permethrin concentration of $0.063.10^{-2}\%$. The coefficient of potentialization of permethrin by crotamiton is thus:

$$\frac{0.072}{0.063 \cdot 10^{-2}} = 113.$$

Moreover, as these two molecules have a different mechanism of action, this new combination should make it possible to avoid phenomena of resistance to pediculicides.

3. Pharmaceutical and Clinical

The new pediculicidal preparations according to the present invention make it possible to produce a new generation of specialty pharmaceuticals having the following advantages:

Outstanding activity against lice and nits

To avoid the usual resistance phenomena

Better effectiveness/toxicity ratio

Advantageous additional activity of crotamiton (antipruriginous)

Possibility of international registration (F.D.A. active ingredients).

The clinical tests carried out on these new preparations confirm the excellent results obtained in the laboratory.

The following formulations are mentioned by way of indication:

| | |
|---|---|
| Crotamiton | 1 to 2 g |
| Permethrin | 0.01 to 0.2 g |
| CTAB (at the stearalkonium chloride) | 0.50 g |
| Quaternized guar gum | 0.15 g |
| PVA/VA (70/30) | 2 g |
| PVP/Dimethyl aminoethyl-methacrylate | 0.50 g |
| 95° Alcohol | 15 to 20 ml |
| Ethoxylated fatty alcohol (20 to 30 EO) | 1 g |
| Fragrance | q.s. |
| Demineralized water q.s. for | 100 g |
| Filling for 100 g: | |
| Emulsified base | 90 g |
| Butane/isobutane/propane mixture | 10 g |

3.2. - Liquid Shampoo

| | |
|---|---|
| Crotamiton | 0.1 to 2 g |
| Bioallethrin | 0.01 to 0.2 g |
| Magnesium alkyl ether sulfate (30%) | 20 g |
| Sorbitan monolaurate (2 EO) | 15 g |
| Cocamido propyl betaine (30%) | 5 g |
| Coconut fatty acid diethanolamide | 4 g |
| Preserving agent | q.s. |
| Fragrance | q.s. |
| Demineralized water q.s. for | 100 ml |

3.3. - Aerosol

| | |
|---|---|
| Crotamiton | 0.1 to 2 g |
| Resmethrin | 0.01 to 0.2 g |
| Silicone oil high volatility | 15 g |
| Deodorized petroleum oil | 15 g |
| Essence of myrth | 0.30 g |
| Butane 3.2 propellant gas q.s. for | 100 ml |
| or | |
| Compressed (N$_2$) propellant gas q.s. | |

3.4. - Two-Phase Shampoo

| | |
|---|---|
| Crotamiton | 0.1 to 2 g |
| Tetramethrin | 0.01 to 0.2 g |
| Isopropyl palmitate | 3 g |
| Volatile cyclic silicone | 5 g |
| Essence of myrth | 0.30 g |
| Cocoamphocarboxyglycinate (40%) | 19 g |
| Sodium alkyl ether sulfate (30%) | 26 g |
| Polymer of polyglycol polyamine | 0.50 g |
| Citric acid q.s. pH | 7 g [sic] |
| Demineralized water q.s. for | 100 ml |

3.5. - 2-Phase Antilice Hair Lotion

| | |
|---|---|
| Solution or pump spray | |
| Crotamiton | 0.1 to 2 g |
| Deltamethrin | 0.01 to 0.2 g |
| Hexamethyl disiloxane | 9 ml |
| Essence of myrth | 0.50 g |
| Lauryl pyridinium chloride | 0.015 g |
| Dimethicone copolyol | 0.15 g |
| Allantoin | 0.05 g |
| N-(Hydroxyethyl)acetamide (70%) | 1 g |
| D-Panthenol | 0.02 g |
| 95° Alcohol | 35 ml |
| Demineralized water q.s. for | 100 ml |

3.6. Nit-Killing Disentangling Balm

| | |
|---|---|
| Crotamiton | 0.1 to 2 g |
| Permethrin | 0.01 to 0.2 g |
| Stearamine oxide | 7.5 g |
| Hcl/Kcl | q.s. |
| Dimethicone copolyol | 0.75 g |
| Hydroxypropyl cellulose | 0.30 g |
| Stearalkonium chloride | 0.25 g |
| Mineral oil | 2.5 g |
| Water q.s. for | 100 g |

We claim:

1. A dermatological or cosmetological composition for the treatment of pediculosis comprising: synergistically effective amounts of crotamiton and permethrin in a weight ratio of 69.5:1 to 11.6:1 and containing from 0.01 to 0.2% by weight of permethrin.

2. The composition of claim 1 containing from 0.1 to 2% by weight of crotamiton.

3. The composition of claim 1 comprising:
a) 0.01 to 1% by weight of said pyrethroid pediculicide,
b) 0.1 to 10% by weight of crotamiton,
c) 0 to 70% by weight of a surface-active agent,
d) 0 to 50% by weight of an organic solvent selected from the group consisting of lower aliphatic alcohols, silicones, deodorized petroleum oil and mixtures thereof,
e) 0 to 4% by weight of a foaming agent,
f) a fragrance,
g) a preserving agent, and
h) water.

* * * * *